US00PP37029P2

(12) United States Plant Patent
Nishikawa

(10) Patent No.: US PP37,029 P2
(45) Date of Patent: Oct. 14, 2025

(54) ***DELOSPERMA* PLANT NAMED 'T2173'**

(50) Latin Name: *Delosperma nubigenum*
Varietal Denomination: T2173

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 19/189,152

(22) Filed: Apr. 24, 2025

(30) Foreign Application Priority Data

Nov. 20, 2024 (QZ) ..... PBR 20242716

(51) Int. Cl.
*A01H 6/30* (2018.01)
*A01H 5/02* (2018.01)

(52) U.S. Cl.
USPC ..... Plt./422

(58) Field of Classification Search
USPC ..... Plt./422
CPC ..... A01H 6/30; A01H 5/02
See application file for complete search history.

*Primary Examiner* — Keith O. Robinson
(74) *Attorney, Agent, or Firm* — Penny J. Aguirre

(57) ABSTRACT

A new cultivar of *Delosperma* plant named 'T2173' that is characterized by its y large flowers, its long flowering period; blooming from early summer to early autumn, its violet purple flowers with white centers, its low-growing plant habit, its high flower count, and its high petal count per flower.

2 Drawing Sheets

Botanical classification: *Delosperma nubigenum.*
Variety denomination: 'T2173'.

BACKGROUND OF THE INVENTION

The present invention relates to a new and distinct cultivar of *Delosperma* plant, botanically known as *Delosperma nubigenum* 'T2173' and will be referred to hereinafter by its cultivar name, 'T2173'. The new cultivar of *Delosperma* is an evergreen perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with compact plant habits, floriferous blooming habits, and large flowers in a unique range of flower colors.

'T2173' was selected in the Inventor's trial garden in May of 2018 as a single unique plant from amongst the seedlings derived from crosses between unnamed and unpatented plants from the Inventor's breeding program.

Asexual propagation of the new cultivar was first accomplished by stem cuttings in September of 2018 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'T2173' as a unique cultivar of *Delosperma.*

1. 'T2173' exhibits very large flowers.
2. 'T2173' exhibits a long flowering period; blooming from early summer to early autumn.

3. 'T2173' exhibits violet purple flowers with white centers.
4. 'T2173' exhibits a low-growing plant habit.
5. 'T2173' exhibits a high flower count.
6. 'T2173' exhibits a high petal count per flower.

Both the female and male parents are similar to 'T2160' in having flowers with similar coloration. The female parent differs from 'T2160' in having a more vigorous growth habit. The male parent differs from 'T2160' in having a more compact plant habit. 'T2173' can be most closely compared to the *Delosperma* cultivars 'T1854' (U.S. Plant Patent No. 34,730) and 'P15R1' (U.S. Plant Pat. No. 31,674). 'T1854' is similar to 'T2173' in having a low growing plant habit, and a high flower count. 'T1854' differs from 'T2173' in having flowers that are pink-purple in color with less distinct centers. 'P15R1' is similar to 'T2173' in having a low-growing plant habit and a high flower count. 'P15R1' differs from 'T2173' in having flowers that are smaller in size and lighter violet purple in color and have less petals per flower, and in having a less dense growth habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102 (b) (1) for disclosure and/or sales prior to the filing date but less than one year prior to the effective filing date. Website listings include listings by Garden Crossings, Plant Addicts, Darwin Perennials, Ball Seed Company, Proven Winners, Creekside Gardens, Classy Groundcovers, Monrovia, Bloomables, Moan Nursery, Phoenix Perennials, Emerald Coast Growers, Griffin Greenhouse Supply, Garden Center Marketing, QVCtv, Mississippi State University, James Greenhouses, Germania Seed, Westcan Greenhouses, and Plantipp.

BRIEF DESCRIPTION OF THE DRAWINGS

The accompanying color photographs illustrate the overall appearance and distinct characteristics of the new *Delosperma*. The photographs were taken of a plant about 1 year in age (from a plug) as grown in an unheated greenhouse in a 17-cm container in Waddinxveen, The Netherlands.

The photograph in FIG. 1 provides a top view of 'PPC093' in bloom.

Figure 1:
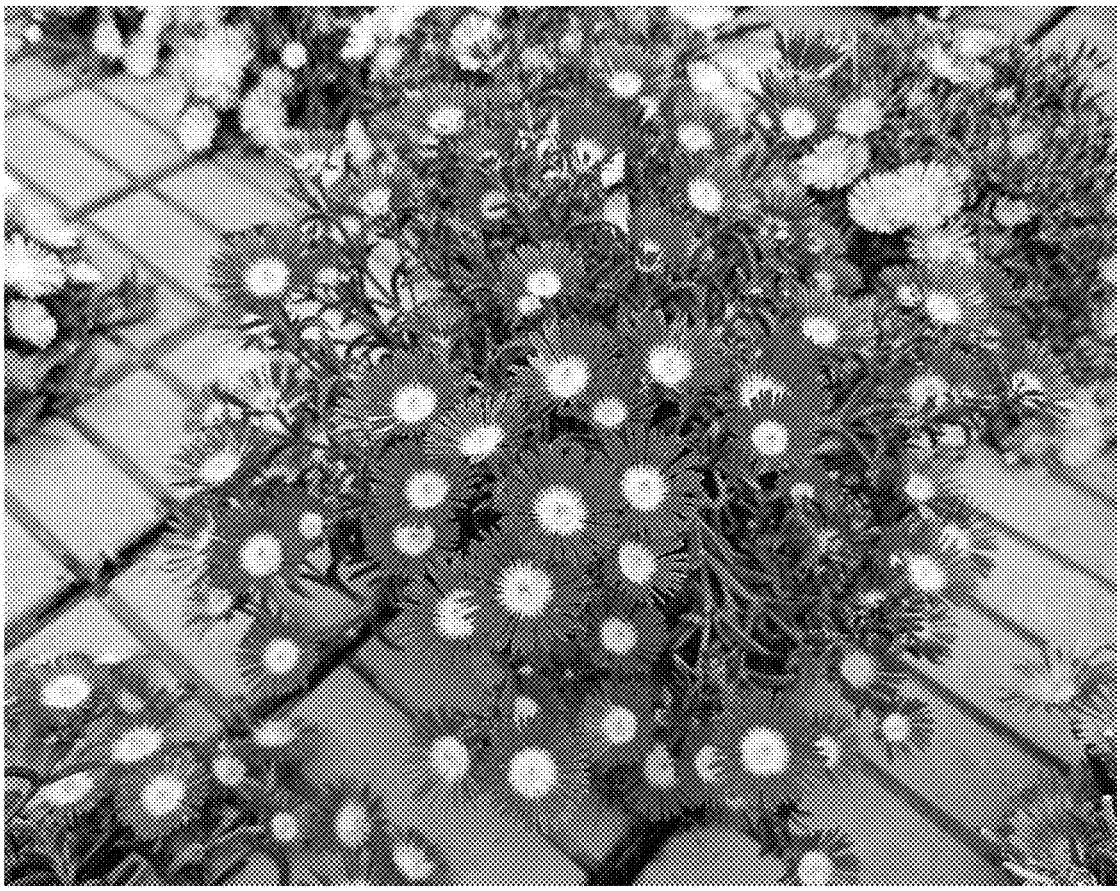
Figure 2:
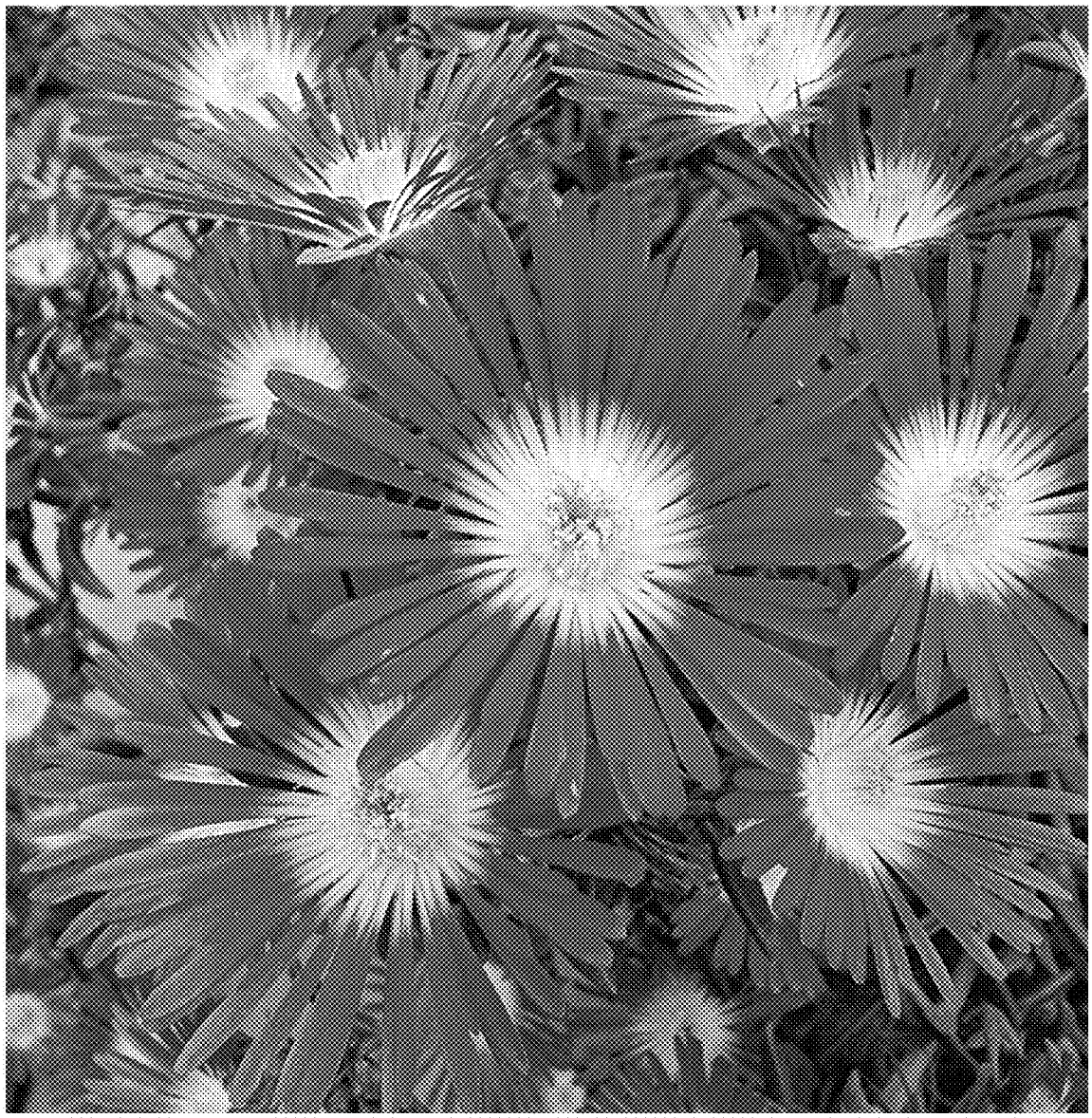

The photograph in FIG. 2 provides a view of the flowers of 'PPC093'.

The colors in the photographs may differ slightly from the color values cited in the detailed botanical description, which accurately describe the colors of the new *Delosperma*.

DETAILED BOTANICAL DESCRIPTION

The following is a detailed description of 1.5-year-old plants of the new cultivar as grown in 17-cm containers in an unheated greenhouse in Waddinxveen, Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period*.—Blooms from early summer to early autumn in The Netherlands.

*Plant type*.—Evergreen perennial.

*Plant habit*.—Flattened, prostrate.

*Height and spread*.—Reaches an average of 11 cm in height and about 32 cm in width as grown in a container, reaches 11 cm in height and 34 to 40 cm in width as grown in the landscape.

*Cold hardiness*.—At least in U.S.D.A. Zone 7.

*Diseases and pests*.—No susceptibility or resistance to diseases or pests has been observed.

*Root description*.—Fibrous roots, primarily 161D in color.

*Propagation*.—Stem cuttings.

*Root development*.—8 weeks for root initiation, 4 months from a rooted cutting to produce a young plant in a P9 container.

*Growth rate and vigor*.—Moderate.

Stem description:

*Shape*.—Round.

*Stem color*.—N244A and 152C, older stems 145A, 245C, and 183A.

*Stem size*.—Lateral branches; an average of 10 cm in length and 4 mm in diameter.

*Internode length*.—An average of 2.5 cm.

*Stem substance*.—Succulent.

*Stem surface*.—Moderately glossy, moderately pubescent.

*Branching habit*.—Freely branching both basal stem, an average of 12 lateral branches per stem.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, sparsely to moderately pubescent.

*Leaf color*.—145A to 145B, middle and tip 137A.

*Leaf size*.—6.2 cm in length and 9 mm in width.

*Leaf quantity*.—Average of 12 per lateral branch.

*Leaf attachment*.—Sessile.

Inflorescence description:

*Inflorescence type*.—Flowers solitary, terminal.

*Flower number*.—An average of 2 per lateral stem, 26 open flowers per plant.

*Flower fragrance*.—None.

*Flower aspect*.—Outward to upright.

*Flower longevity*.—Average of 4 days self-cleaning.

*Flower type*.—Single.

*Flower size*.—Average of 5 cm in diameter and 1.2 cm in depth.

*Flower buds*.—Broadly ovate to oblong in shape, an average of 1 cm in length and 7 mm in diameter, NN78A in color, surface texture is smooth and glossy with the sepal portion smooth and dull.

*Calyx*.—Rotate in shape, 8 to 9 mm in depth and 2.8 cm in diameter.

*Sepals*.—5, rotate, ovate in shape, margin entire, an average of 1 cm in length and 6 mm in width, broadly acute apex, broadly cuneate base, surface is glandular, color upper and lower surface 137A.

*Petals*.—An average of 60 to 70 per flower, rotate, oblanceolate in shape, surface is smooth and glossy on both surfaces, margin entire, apex obtuse, base cuneate, an average of 2.1 cm in length and 2.5 mm in width, color when opening and fully open upper and lower surface; NN78A with stripe 78A and NN155A.

*Petaloids*.—An average of 20 per flower, rotate and near vertical surrounding stamens, lanceolate in shape, glossy on both surfaces, entire margins, apex obtuse, base truncate, an average of 1 cm in length and 1 mm in width, color: upper and lower NN155A, tips NN78D.

*Peduncle*.—Average of 3 cm in length and 3 mm in diameter, straight on top of lateral branch at 0°, color; 144B with 145A to 145B and 183A, surface moderately glossy, sparsely to moderately pubescent.

*Pedicel*.—None.

Reproductive organs:

*Pistils*.—5, an average of 3 mm in length, stigma; triangular shaped, style and stigma; (not distinguishable) combined an average of 2 mm in length and 151A in color, ovary; 143C in color.

*Stamens*.—Average of 60, 12A in color, anthers; dorsifixed and narrowly oblong in shape, an average of 0.5 mm in diameter, filaments; 5 mm in length, NN155A and 14B in color, anthers; NN155A in color, pollen; moderate in quantity and 6A in color.

*Fruit*.—Fruit and seed production was not observed under the conditions tested.

It is claimed:

1. A new and distinct variety of *Delosperma* plant named 'T2173' as described and illustrated herein.

* * * * *